United States Patent
Nakata et al.

(10) Patent No.: US 10,234,418 B2
(45) Date of Patent: Mar. 19, 2019

(54) GAS SENSOR CONTROL DEVICE

(71) Applicant: DENSO CORPORATION, Kariya, Aichi-pref. (JP)

(72) Inventors: Shingo Nakata, Kariya (JP); Mikiyasu Matsuoka, Kariya (JP); Yasuo Mukai, Kariya (JP)

(73) Assignee: DENSO CORPORATION, Kariya (JP)

( * ) Notice: Subject to any disclaimer, the term of this patent is extended or adjusted under 35 U.S.C. 154(b) by 422 days.

(21) Appl. No.: 15/023,435

(22) PCT Filed: Sep. 25, 2014

(86) PCT No.: PCT/JP2014/004902
§ 371 (c)(1),
(2) Date: Mar. 21, 2016

(87) PCT Pub. No.: WO2015/045380
PCT Pub. Date: Apr. 2, 2015

(65) Prior Publication Data
US 2016/0202210 A1    Jul. 14, 2016

(30) Foreign Application Priority Data
Sep. 27, 2013   (JP) ................................ 2013-202131

(51) Int. Cl.
*G01N 27/417* (2006.01)
*G01N 27/416* (2006.01)
(Continued)

(52) U.S. Cl.
CPC ....... *G01N 27/4163* (2013.01); *F02D 41/123* (2013.01); *F02D 41/1454* (2013.01);
(Continued)

(58) Field of Classification Search
CPC ................................................ G01N 27/4065
See application file for complete search history.

(56) References Cited

U.S. PATENT DOCUMENTS

| 4,741,817 A |   | 5/1988 | Croset et al. |
|---|---|---|---|
| 5,340,462 A | * | 8/1994 | Suzuki ................ F02D 41/1481 |
|   |   |   | 123/688 |

(Continued)

FOREIGN PATENT DOCUMENTS

| JP | 59-215935 | 12/1984 |
|---|---|---|
| JP | 59-226251 | 12/1984 |

(Continued)

OTHER PUBLICATIONS

EPO computer-generated English language translation of the Description section of JP 2007-278732 A, downloaded Jul. 11, 2018, patent published Oct. 25, 2007. (Year: 2007).*

(Continued)

*Primary Examiner* — Alexander S Noguerola
(74) *Attorney, Agent, or Firm* — Nixon & Vanderhye P.C.

(57) ABSTRACT

An $O_2$ sensor includes a sensor element using a solid electrolyte layer and a pair of electrodes placed at a position to interpose the solid electrolyte layer, detects an exhaust gas from an internal combustion engine as an object of a detection, and outputs an electromotive force signal depending on an air-fuel ratio of the exhaust gas. The sensor element is connected with a constant current circuit supplying a constant current that is prescribed. A microcomputer conducts an abnormality diagnosis of an output response of the sensor element on the basis of a state of variation in an electromotive force output. Further, when the microcomputer conducts the abnormality diagnosis, the microcomputer restricts a supply of the constant current by the constant current circuit before conducting the abnormality diagnosis.

4 Claims, 10 Drawing Sheets

(51) Int. Cl.
    *G01N 27/407*     (2006.01)
    *G01N 33/00*     (2006.01)
    *G01N 27/406*     (2006.01)
    *G01N 27/409*     (2006.01)
    *F02D 41/12*     (2006.01)
    *F02D 41/14*     (2006.01)

(52) U.S. Cl.
    CPC ....... *F02D 41/1495* (2013.01); *G01N 27/409* (2013.01); *G01N 27/4065* (2013.01); *G01N 27/4071* (2013.01); *G01N 33/007* (2013.01); *G01N 33/0073* (2013.01)

(56) References Cited

U.S. PATENT DOCUMENTS

| | | |
|---|---|---|
| 2012/0043205 A1 | 2/2012 | Matsuoka et al. |
| 2014/0373512 A1 | 12/2014 | Yokoi et al. |
| 2015/0025778 A1 | 1/2015 | Matsuoka et al. |

FOREIGN PATENT DOCUMENTS

| | | |
|---|---|---|
| JP | 60-98141 | 6/1985 |
| JP | 2007-278732 | 10/2007 |
| JP | 4055476 | 12/2007 |

OTHER PUBLICATIONS

Mishima et al., copending U.S. Appl. No. 15/023,446, filed Mar. 21, 2016.
Mishima et al., copending U.S. Appl. No. 15/023,441, filed Mar. 21, 2016.
International Search Report for PCT/JP2014/004902 dated Dec. 22, 2014, 3 pages.
Written Opinion of the ISA for PCT/JP2014/004902 dated Dec. 22, 2014, 8 pages.

* cited by examiner

FIG. 12
(a) DELAY TIME
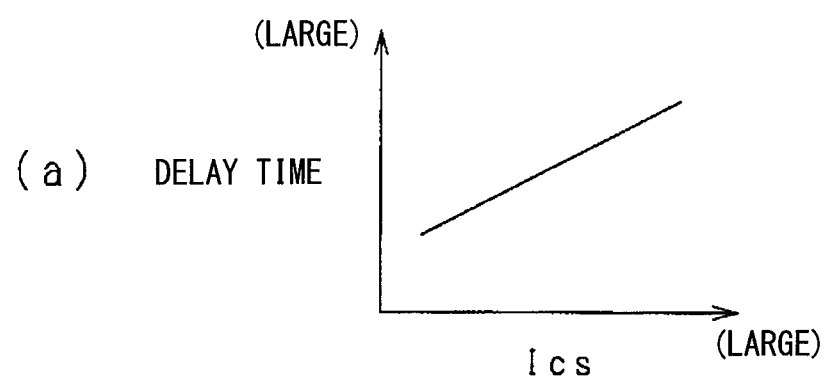
(b) DELAY TIME
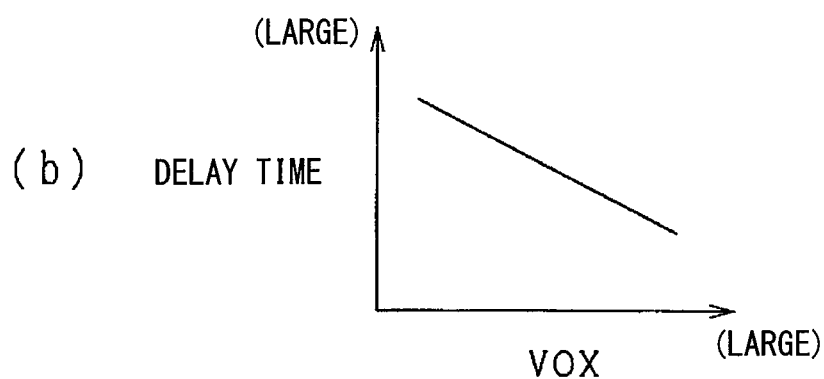

GAS SENSOR CONTROL DEVICE

CROSS REFERENCE TO RELATED APPLICATION

This application is the U.S. national phase of International Application No. PCT/JP2014/004902 filed on Sep. 25, 2014 which designated the U.S. and claims priority to Japanese Patent Application No. 2013-202131 filed on Sep. 27, 2013, the entire contents of each of which are hereby incorporated by reference.

TECHNICAL FIELD

The present disclosure relates to a gas sensor control device.

BACKGROUND ART

For example, a vehicle engine generally uses an electromotive force output type gas sensor which takes the exhaust gas discharged from the engine as an object of detection and detects the oxygen concentration. The gas sensor has an electrogenic cell which outputs an electromotive force signal which differs depending on whether the exhaust gas air-fuel ratio is rich or lean. Specifically, when the air-fuel ratio is rich, the gas sensor outputs an electromotive force signal of about 0.9 V and when the air-fuel ratio is lean, the gas sensor outputs an electromotive force signal of about 0 V.

As for this kind of gas sensor, attention has been drawn to the fact that when the air-fuel ratio of the exhaust gas changes to rich or lean, the sensor output changes with a delay from the actual change of the air-fuel ratio. Various techniques have been described to improve this output characteristic.

For example, in the gas sensor control device in Patent Literature 1, a constant current circuit is connected to at least one of a pair of sensor electrodes. When it is determined that a change request to change the output characteristic of the gas sensor has been generated, the direction of constant current is determined according to the change request and the constant current circuit is controlled so that the constant current flows in the determined direction. Thus, the output characteristic of the gas sensor is appropriately controlled by supplying the constant current.

On the other hand, the document describes a technique of conducting abnormality diagnosis of the gas sensor. For example, when sensor output varies, abnormality diagnosis concerning output response is conducted according to the amount of output variation (variation speed) within a given time period. However, in the above arrangement that a constant current flows in the gas sensor, for example, when the air-fuel ratio is controlled on a richer side of the stoichiometric value, sensor output is smaller than when no constant current flows (namely, the sensor output is closer to the stoichiometric value of 0.45 V) and as a consequence, the amount of output variation which can be used as a parameter for abnormality diagnosis is small. When the abnormality diagnosis parameter is small, the accuracy of abnormality diagnosis may decrease.

PRIOR ART LITERATURES

Patent Literature

Patent Literature 1: JP2012-63345A

SUMMARY OF INVENTION

The present disclosure has a main object to provide a gas sensor control device which improves the output characteristic of a gas sensor and increases the accuracy of abnormality diagnosis.

According to the present disclosure, a gas sensor control device is applied to a gas sensor which has an electrogenic cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas. The gas sensor control device includes a constant current supplying section supplying a constant current to the electrogenic cell, a control section controlling the constant current supplying section to supply the constant current to the electrogenic cell in order to change an output characteristic of the electrogenic cell, and an abnormality diagnosing section conducting an abnormality diagnosis of an output response of the electrogenic cell on the basis of a state of variation in an electromotive force output, when the electromotive force output of the electrogenic cell varies. When the abnormality diagnosing section conducts the abnormality diagnosis, the control section restricts a supply of the constant current by the constant current supplying section before conducting the abnormality diagnosis.

When the constant current flows in the electrogenic cell, electromotive force output (voltage value) increases or decreases depending on the direction of the constant current even when the air-fuel ratio (oxygen concentration in the exhaust gas) is the same. In this case, while the constant current flows, in conducting abnormality diagnosis of the electrogenic cell according to the mode in which electromotive force output varies (for example, the range of output variation per given time period), the range in which output can vary might be small, resulting in possible decrease in the accuracy of abnormality diagnosis. In this respect, in the above arrangement, since the supply of constant current is restricted before conducting abnormality diagnosis, the range of variation in electromotive force output for abnormality diagnosis can be larger than when the constant current is supplied. For example, when electromotive force output is close to the stoichiometric value due to the supply of constant current, its difference from the stoichiometric value can be increased. Consequently, the desired variation range of electromotive force output can be ensured and the accuracy of abnormality diagnosis can be increased.

Specifically, for example, in the output characteristic graph of FIG. 7, when electromotive force output varies from Y1 to Y2 with change in the characteristic due to the supply of constant current, the electromotive force output can be returned to Y1. Consequently, in conducting abnormality diagnosis according to the state of variation in electromotive force output (the range of variation) when the air-fuel ratio is changed to the lean side, the accuracy of the abnormality diagnosis can be increased.

BRIEF DESCRIPTION OF DRAWINGS

The above and other objects, features and advantages of the present disclosure will become more apparent from the following detailed description made with reference to the accompanying drawings. In the drawings:

FIG. 12 is a graph which shows the relation among delay time, constant current, and sensor electromotive force.

DESCRIPTION OF EMBODIMENTS

Figure 1:
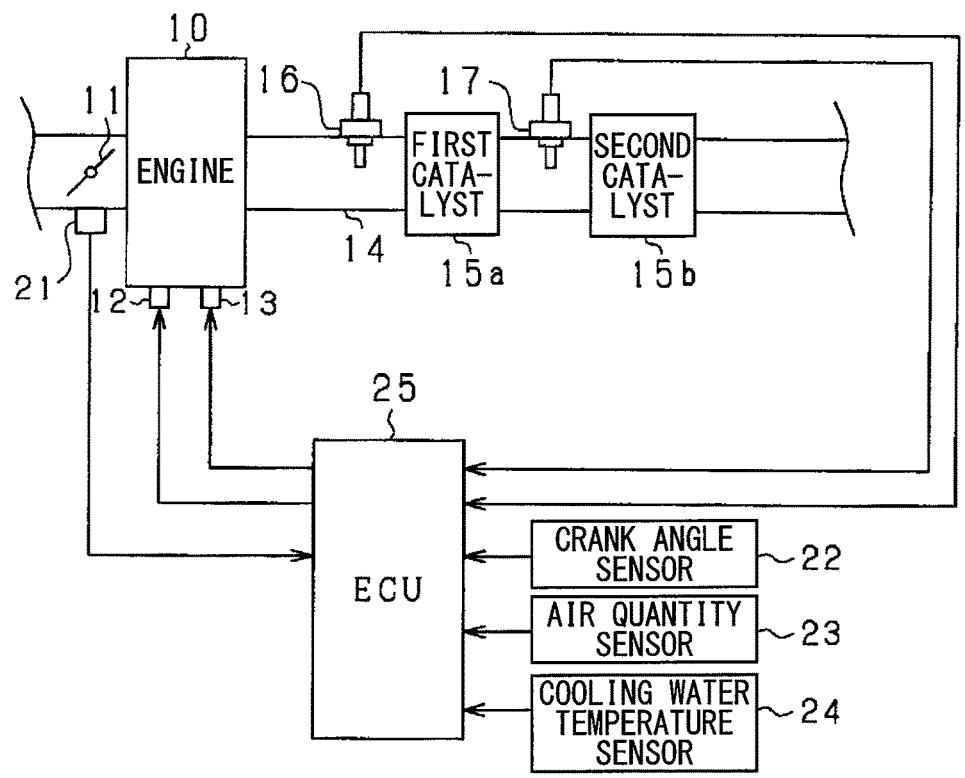
FIG. 1 is a schematic diagram which shows the general configuration of an engine control system.

Next, an embodiment of a gas sensor control device according to the present disclosure will be described referring to drawings. This embodiment concerns an engine control system which uses a gas sensor located on the exhaust pipe of an on-vehicle engine (internal combustion engine) to perform various controls, etc. of the engine according to output of the gas sensor. The control system, centered on an electronic control unit (ECU), performs control of the amount of fuel injection, control of ignition timing and so on. FIG. 1 is a block diagram which shows the general configuration of the system.

In FIG. 1, an engine 10 is, for example, a gasoline engine which includes a throttle valve 11 that is electronically controlled, a fuel injection valve 12, and an ignition device 13. An exhaust pipe 14 of the engine 10 is provided with catalysts 15a and 15b as exhaust gas purifying devices. The exhaust pipe 14 corresponds to an exhaust section. The catalysts 15a and 15b are, for example, both three-way catalysts; the catalyst 15a is a first catalyst as an upstream catalyst and the catalyst 15b is a second catalyst as a downstream catalyst. As widely known, a three-way catalyst purifies three major emission toxic components, carbon monoxide (CO), hydrocarbon (HC), and nitrogen oxide (NOx) such as NO, and is structured so that metal such as platinum, palladium, or rhodium is supported by a honeycomb or lattice-shaped ceramic support. In this case, the three-way catalyst purifies CO and HC as rich components by oxidation action and NOx as a lean component by reduction action.

An A/F sensor 16 is located upstream of the first catalyst 15a and an $O_2$ sensor 17 is located between the catalysts 15a and 15b (downstream of the first catalyst 15a and upstream of the second catalyst 15b). The A/F sensor 16 outputs an A/F signal which is roughly proportional to the air-fuel ratio of the exhaust gas. The $O_2$ sensor 17 also outputs an electromotive force signal which differs depending on whether the air-fuel ratio of the exhaust gas is lean or rich.

The system further includes various sensors including a throttle opening sensor 21 which detects the opening of the throttle valve 11, a crank angle sensor 22 which outputs a rectangular crank angle signal at every prescribed crank angle of the engine, an air quantity sensor 23 which detects the quantity of intake air in the engine 10, and a cooling water temperature sensor 24 which detects the temperature of engine cooling water. In addition to the above, the system includes a combustion pressure sensor which detects the combustion pressure in the cylinder, an accelerator opening sensor which detects the opening of the accelerator (amount of operation of the accelerator), and an oil temperature sensor which detects the temperature of engine lubricant, though not shown in the figure. In this embodiment, the prescribed crank angle is 30° CA cycle. These sensors correspond to an operation condition detecting section.

An ECU 25 is mainly comprised of a known microcomputer 41 which includes a CPU, ROM, and RAM, and executes various control programs stored in the ROM to perform various controls of the engine 10 depending on each engine operation condition. In other words, the ECU 25 receives signals from the above various sensors, etc. and calculates the amount of fuel injection and ignition timing according to the various signals to control the drive of the fuel injection valve 12 and the ignition device 13.

In connection with the amount control of fuel injection, the ECU 25 performs air-fuel ratio feedback control according to a detection signal from the A/F sensor 16 on the upstream of the first catalyst and a detection signal from the $O_2$ sensor 17 on the downstream of the first catalyst. Specifically, the ECU 25 performs main feedback control so that the actual air-fuel ratio (actual air-fuel ratio on the catalyst upstream side) detected by the A/F sensor 16 becomes a target air-fuel ratio set according to the engine operation condition, and also performs sub-feedback control so that the actual air-fuel ratio (actual air-fuel ratio on the catalyst downstream side) detected by the $O_2$ sensor 17 becomes the target air-fuel ratio. In sub-feedback control, for example, according to the difference between the actual air-fuel ratio on the catalyst downstream side and the target air-fuel ratio, the target air fuel ratio in main feedback control is modified or the amount of feedback correction in the main feedback control is modified. For air-fuel ratio control, for example, the ECU 25 performs stoichiometric feedback to make the target air-fuel ratio stoichiometric or nearly stoichiometric. In this case, stoichiometry is equivalent to a theoretical air-fuel ratio.

The ECU 25 performs fuel cut on a fuel cut condition, for example, that the accelerator pedal of a vehicle is released (accelerator is off). In this case, fuel injection and ignition are both stopped while fuel cut is underway.

Figure 2:
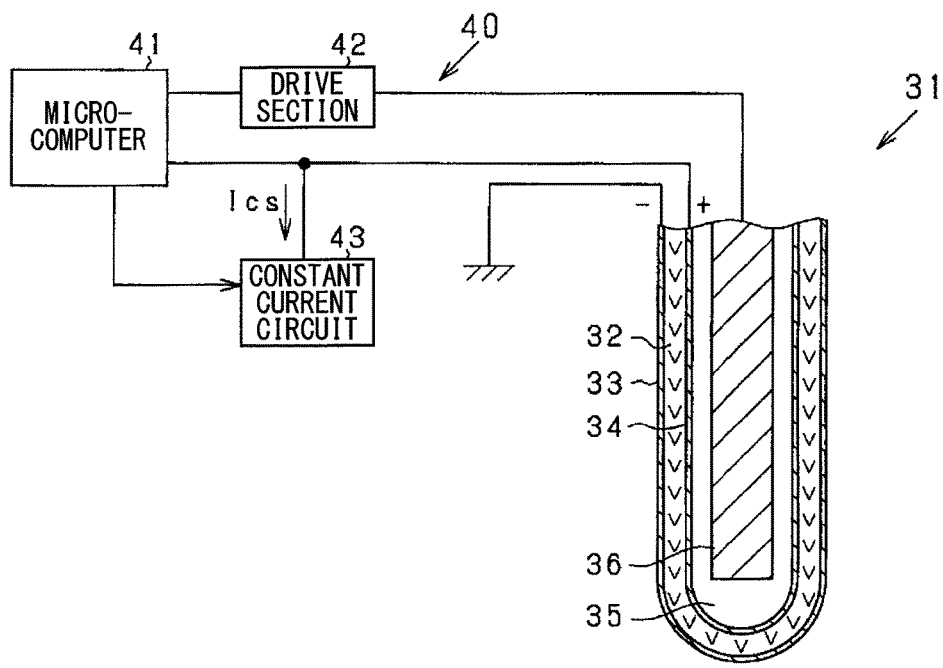
FIG. 2 is a diagram which shows the cross-sectional structure of a sensor element and the general structure of a sensor control section.

Next, the structure of the $O_2$ sensor 17 on the downstream of the first catalyst will be described. The $O_2$ sensor 17 has a sensor element 31 with a cup-shaped structure. FIG. 2 shows the cross-sectional structure of the sensor element 31. Specifically, the sensor element 31 has a roughly U-shaped cross section. Actually, the sensor element 31 is entirely housed in a housing or element cover and installed in the engine exhaust pipe. The sensor element 31 corresponds to an electrogenic cell.

The sensor element 31 has a solid electrolyte layer 32 with a roughly U-shaped cross section and an exhaust side electrode 33 on its outer surface and an air side electrode 34 on its inner surface. These electrodes 33 and 34 lie as layers on the surfaces of the solid electrolyte layer 32. The solid electrolyte layer 32 has an oxygen ion-conductive sintered oxide made by dissolving CaO, MgO, Y2O3, Yb2O3 or the like as a stabilizer in $ZrO_2$, $HfO_2$, $ThO_2$, $Bi2O3$ or the like. The electrodes 33 and 34 are both made of a catalytically active precious metal such as platinum and have a porous chemical coating or the like on their surfaces. The electrodes 33 and 34 are a pair of opposite electrodes and also called sensor electrodes. The inner space surrounded by the solid electrolyte layer 32 is an air chamber 35, and a heater 36 is housed in the air chamber 35. The air chamber 35 is also called the reference chamber. The heater 36 has a sufficient heat generating capacity to activate the sensor element 31 and heats the entire sensor element with its generated heat energy. The activation temperature of the $O_2$ sensor 17 is, for example, about 500 to 650° C. The inside of the air chamber 35 is maintained at a prescribed oxygen concentration by introduction of the air.

In the above sensor element 31, the outer side of the solid electrolyte layer 32 which is near the exhaust side electrode 33 has an exhaust gas atmosphere and the inner side of the solid electrolyte layer 32 which is near the air side electrode 34 has an air atmosphere, and depending on the oxygen concentration difference (oxygen partial pressure difference) between them, an electromotive force is generated between the electrodes 33 and 34. In short, an electromotive force which differs depending on whether the air-fuel ratio is rich or lean is generated. In this case, the exhaust side electrode 33 is lower in oxygen concentration than the air side electrode 34 as the reference electrode and in the sensor element 31, an electromotive force is generated with the air side electrode 34 as the positive side and the exhaust side electrode 33 as the negative side. Consequently, the $O_2$ sensor 17 outputs an electromotive force signal which depends on the oxygen concentration of the exhaust gas (namely, air-fuel ratio).

Figure 3:
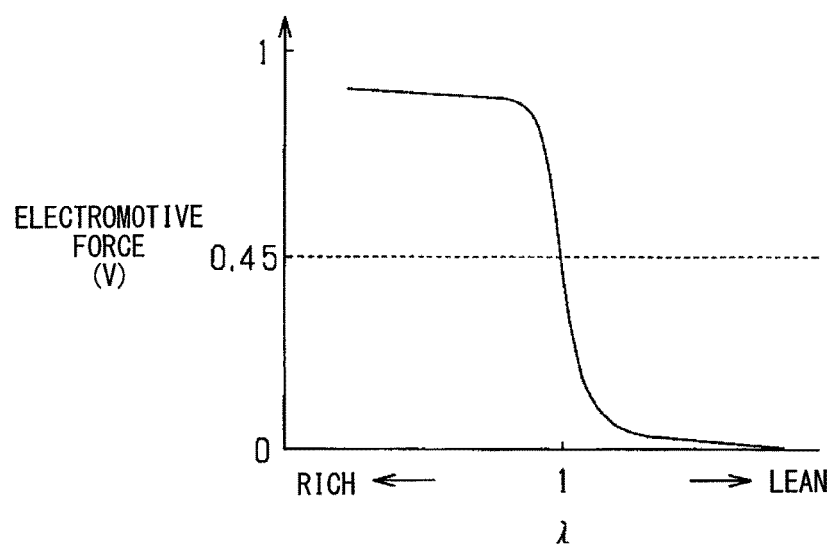
FIG. 3 is an electromotive force characteristic graph which shows the relation between excess air ratio and the electromotive force of the sensor element.

FIG. 3 is an electromotive force characteristic graph which shows the relation between excess air ratio $\lambda$ of the exhaust gas and the electromotive force of the sensor element 31. In FIG. 3, the horizontal axis represents excess air ratio $\lambda$ and when $\lambda$ is 1, the air-fuel ratio of the exhaust gas is stoichiometric. The sensor element 31 generates an electromotive force which differs depending on whether the air-fuel ratio is rich or lean, and has a characteristic that the electromotive force suddenly changes when the ratio is nearly stoichiometric. Specifically, when the ratio is rich, the electromotive force of the sensor element 31 is about 0.9 V and when the ratio is lean, the electromotive force of the sensor element 31 is about 0 V.

In FIG. 2, a sensor control section 40 is connected to the sensor element 31 and when an electromotive force is generated in the sensor element 31 depending on the air-fuel ratio (oxygen concentration) of the exhaust gas, a sensor detection signal (electromotive force signal) equivalent to the electromotive force is sent to a microcomputer 41 in the sensor control section 40. The microcomputer 41 calculates the air-fuel ratio according to the electromotive force signal from the sensor element 31. The sensor control section 40 is located in the ECU 25 shown in FIG. 1. In the ECU 25, the microcomputer 41 is provided as a calculating section which has an engine control function and a sensor control function. In this case, the microcomputer 41 calculates the engine rotation speed and the intake air amount according to the results of detection by the above various sensors. Alternatively, in the ECU 25, a microcomputer for engine control and a microcomputer for sensor control may be provided separately.

The microcomputer 41 makes a determination about the activity state of the sensor element 31 and also controls drive of the heater 36 through a drive section 42 according to the result of the determination. Since the activity determination and heater control are well known, the activity determination and heater control are briefly described below. The microcomputer 41 changes the voltage or current applied to the sensor element 31 in an alternating manner and detects the resulting current variation or voltage variation. Then, the element resistance (element impedance) of the sensor element 31 is calculated according to the current variation or voltage variation and also energization of the heater 36 is controlled according to the element resistance. At this time, the activity state (namely, element temperature) of the sensor element 31 is correlated with the element resistance. By controlling the element resistance to a given target value, the sensor element 31 is maintained in the desired activity state. In the desired activity state, the activation temperature of the sensor element 31 is 500 to 650° C. For heater control, it is desirable to perform, for example, element temperature feedback control.

In operation of the engine 10, the actual air-fuel ratio of exhaust gas changes sequentially and in some cases the actual air-fuel ratio changes between rich and lean cyclically. When the actual air-fuel ratio changes in this way, when there is a response gap in the relation between output of the $O_2$ sensor 17 and the presence of $NO_x$ as a lean component ($NO_x$ purification range), the gap may affect the emission performance at each time. For example, the quantity of $NO_x$ in the exhaust gas may increase during high-load operation of the engine 10 (during vehicle acceleration).

Figure 4:
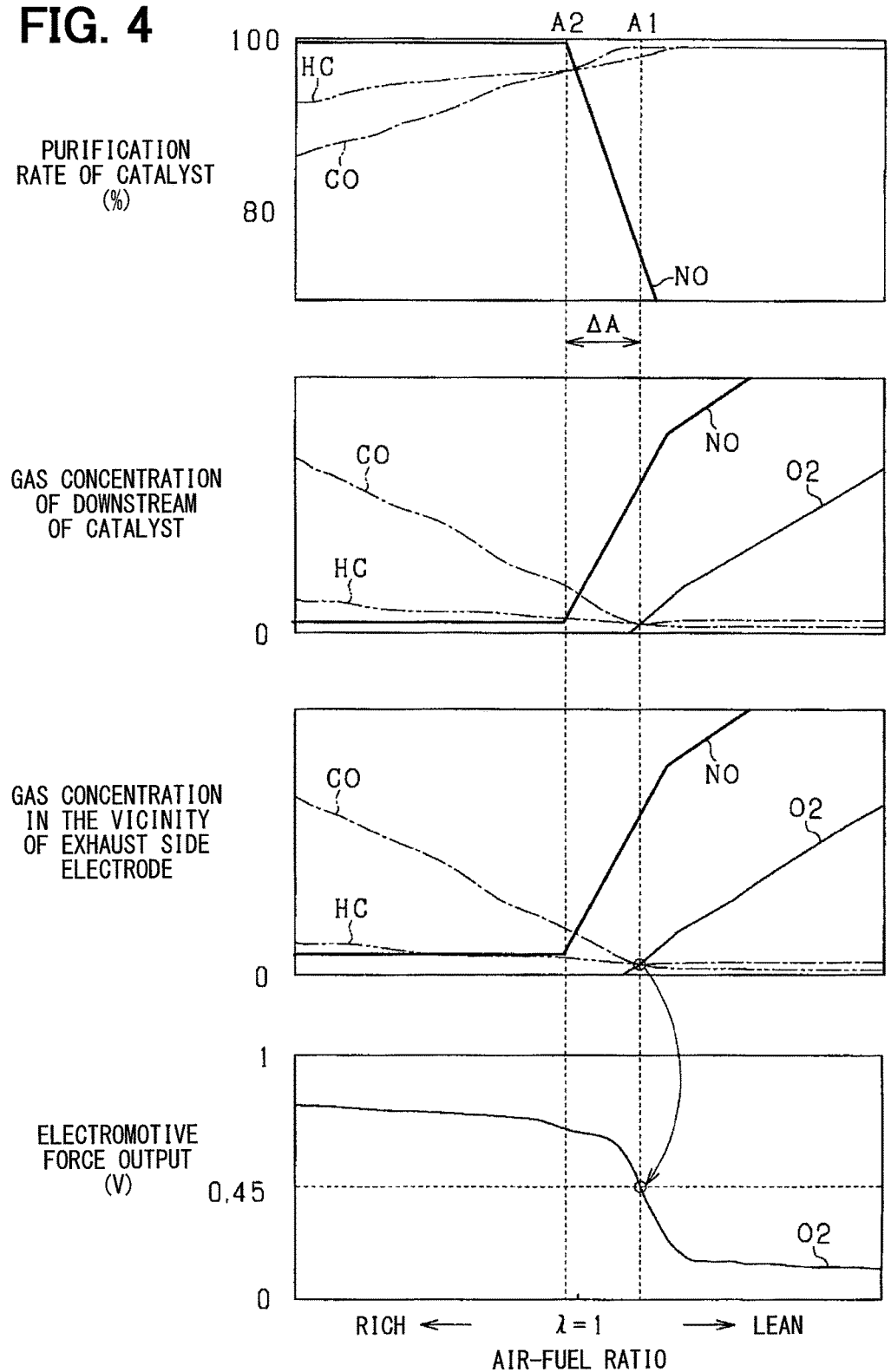
FIG. 4 shows graphs which show the purification characteristic of a first catalyst and the output characteristic of an $O_2$ sensor.

In this embodiment, the state of detection by the $O_2$ sensor 17 is changed according to the relation between the output characteristic of the electromotive force output type $O_2$ sensor 17 and the exhaust gas purification characteristic of the first catalyst 15a located upstream thereof. FIG. 4 shows graphs of the purification characteristic of the first catalyst 15a as a three-way catalyst and the output characteristic of the $O_2$ sensor 17. Specifically the graphs respectively show:

the relation between the purification rates of the first catalyst 15a for the three emission toxic components CO, HC and $NO_x$, and air-fuel ratio the relation between the gas concentration and oxygen concentration of the above three components of downstream of the first catalyst 15a, and air-fuel ratio the relation between the gas concentration and oxygen concentration of the above three components in the vicinity of the surface of the exhaust side electrode 33 of the $O_2$ sensor 17, and air-fuel ratio the relation between the electromotive force output of the $O_2$ sensor 17 and air-fuel ratio.

The first catalyst 15a has a purification window in which all the purification rates for the three components become high near the stoichiometric point, as is well known. When the air-fuel ratio is stoichiometric, excess air ratio $\lambda$ is 1. Looking at the concentrations of the three components and oxygen on the catalyst downstream side, while reaction equilibrium point A1 at which the concentrations of the rich components (CO, HC) and the oxygen concentration are equal is present near the stoichiometric point, $NO_x$ outflow point A2 at which $NO_x$ (NO) begins to flow out is present downstream of the catalyst. In this case, the $NO_x$ outflow point A2 is on a richer side of the reaction equilibrium point A1 and there is gap $\Delta A$ between the $NO_x$ outflow point A2 and the reaction equilibrium point A1. In other words, the first catalyst 15a has a purification characteristic that the $NO_x$ outflow point A2 at which $NO_x$ begins to flow out is on a richer side of the reaction equilibrium point A1 as the equilibrium point of the rich components and oxygen. The reaction equilibrium point A1 corresponds to the first air-fuel ratio point and the $NO_x$ outflow point A2 corresponds to the second air-fuel ratio point. It may be said that the reaction equilibrium point A1 is an inflexion point in the equilibrium characteristic of the rich components and oxygen and the $NO_x$ outflow point A2 is an inflexion point in the $NO_x$ outflow concentration characteristic.

When the exhaust gas containing CO, HC, $NO_x$, and $O_2$ is introduced into the first catalyst 15a during operation of the engine, $NO_x$ as well as CO and HC flows out from the first catalyst 15a simultaneously. Taking a closer look, CO, HC and $NO_x$ somewhat flow out, for example, even in the purification window range of the three-way catalyst. In this case, whereas $O_2$ flows out while balancing with CO and HC ($O_2$ begins to flow out with CO and HC concentrations≈0), $NO_x$ flows out to the catalyst downstream independently of the reaction of CO and HC and thus gap ΔA as the difference between reaction equilibrium point A1 and $NO_x$ outflow point A2 is generated.

In addition, the concentrations of the above three components and oxygen in the vicinity of the exhaust side electrode of the $O_2$ sensor 17 are the same as on the catalyst downstream side. In this case, where the concentrations of the three components and oxygen are on a richer side of the reaction equilibrium point A1, there are more rich components (CO, HC) than oxygen, and where the concentrations of the three components and oxygen are on a leaner side of the reaction equilibrium point A1, there is more oxygen than the rich components. Therefore, regarding the electromotive force output of the $O_2$ sensor 17, an electromotive force signal, either a rich signal (0.9 V) or a lean signal (0 V), is outputted with the reaction equilibrium point A1 of the first catalyst 15a as the boundary. In this case, the reaction equilibrium point of the rich components and oxygen in the $O_2$ sensor 17 may be said to correspond to the reaction equilibrium point A1 in the first catalyst 15a. $NO_x$ is also present on a richer side of the reaction equilibrium point A1.

Regarding CO, HC, and $NO_x$ in the exhaust gas, oxidation reaction and reduction reaction take place in the vicinity of the exhaust side electrode of the $O_2$ sensor 17 in accordance with the following formulae:

$$2CO+O_2 \rightarrow 2CO_2 \quad (1)$$

$$CH_4+2O_2 \rightarrow CO_2+2H_2O \quad (2)$$

$$2CO+2NO \rightarrow 2CO_2+N_2 \quad (3)$$

When the equilibrium constants of the above formulae (1) to (3) are expressed by k1, k2, and k3 respectively, the relation of k1, k2>>k3 holds.

In this case, in the $O_2$ sensor 17, equilibrium points are determined by gas reactions of CO, HC, $NO_x$, $O_2$ and so on. In this embodiment, equilibrium points correspond to an electromotive force output of 0.45 V. However, because of the difference among equilibrium constants, the reaction of CO and HC with $O_2$ is the main reaction on the exhaust side electrode 33.

In the exhaust gas purification characteristic of the first catalyst 15a, the above gap ΔA exists and the gap ΔA affects the output characteristic of the $O_2$ sensor 17, so even when $NO_x$ flows out from the first catalyst 15a, output of the $O_2$ sensor 17 does not correspond to the outflow of $NO_x$. For this reason, the outflow of $NO_x$ cannot be recognized and consequently the amount of $NO_x$ emissions may increase.

Figure 5:
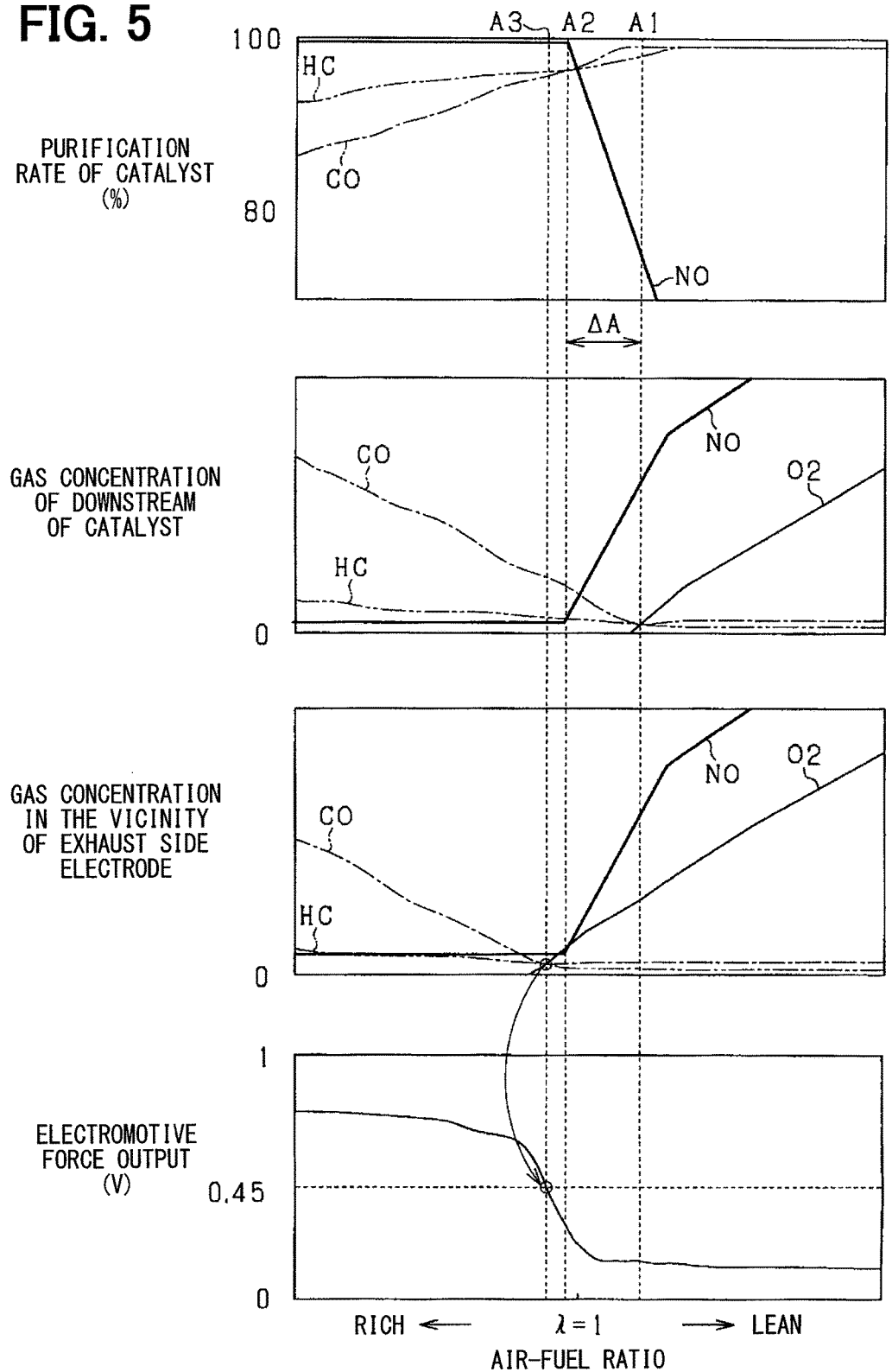
FIG. 5 shows graphs which show the purification characteristic of the first sensor and the output characteristic of the $O_2$ sensor.

Therefore, in this embodiment, a given current is made to flow between the pair of electrodes 33 and 34 in the sensor element 31 of the $O_2$ sensor 17 so as to decrease the rich component concentration and increase the oxygen concentration in the vicinity of the exhaust side electrode of the $O_2$ sensor 17. In short, as shown in FIG. 5, the equilibrium point of gas reaction in the vicinity of the exhaust side electrode of the $O_2$ sensor 17 is changed from reaction equilibrium point A1 to reaction equilibrium point A3. In comparison with FIG. 4, FIG. 5 shows that the concentration characteristics of CO, HC, and $O_2$ in the vicinity of the exhaust side electrode of the $O_2$ sensor 17 are all shifted to the rich side. Consequently the output characteristic of the $O_2$ sensor 17 changes so that when $NO_x$ flows out from the first catalyst 15a, output of the $O_2$ sensor 17 corresponds to the outflow of $NO_x$.

Figure 6:
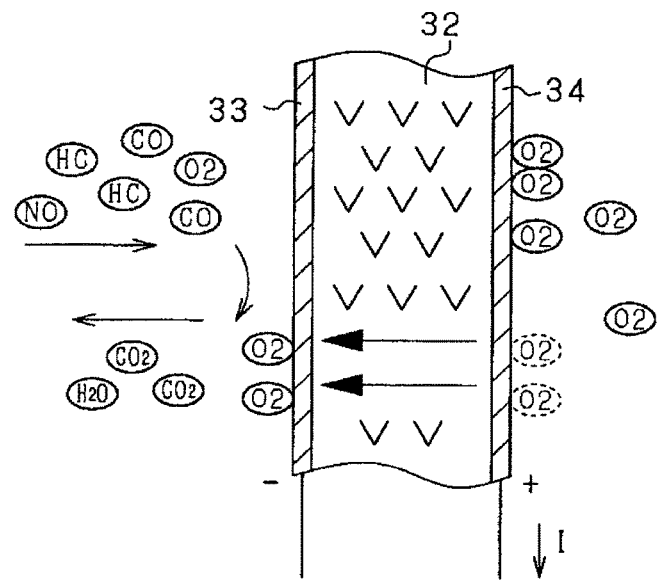
FIG. 6 is a schematic diagram which shows reaction of gas components in the sensor element.

The principle on which the sensor output characteristic is changed by supplying a current between the pair of electrodes 33 and 34 is as follows. As shown in FIG. 6, there are CO, HC, $NO_x$, and $O_2$ in the vicinity of the exhaust side electrode 33 of the $O_2$ sensor 17 and in this condition, a current is supplied to the sensor element 31 so that oxygen ions move from the air side electrode 34 to the exhaust side electrode 33 through the solid electrolyte layer 32. Specifically, oxygen pumping is performed in the sensor element 31. In this case, at the exhaust side electrode 33, the oxygens which have moved to the exhaust side electrode 33 through the solid electrolyte layer 32 react with CO and HC and generate $CO_2$ and $H_2O$. Consequently, CO and HC are removed in the vicinity of the exhaust side electrode 33 and the equilibrium point of gas reaction in the vicinity of the exhaust side electrode 33 of the $O_2$ sensor 17 shifts to the rich side.

Next, the structure of the sensor control section 40 which performs control for the $O_2$ sensor 17 will be described. The structure of the sensor control section 40 is as illustrated in FIG. 2 and the sensor control section 40 has the microcomputer 41 as a control section. The microcomputer 41 receives an electromotive force signal from the sensor element 31 through an A/D converter, etc. and calculates the air-fuel ratio of the exhaust gas according to the electromotive force signal. Alternatively, the microcomputer 41 calculates the air-fuel ratio on the catalyst downstream according to the electromotive force signal. A constant current circuit 43 as a constant current supplying section is connected midway in an electric pathway which electrically connects the air side electrode 34 of the sensor element 31 and the microcomputer 41, and when the sensor element 31 generates an electromotive force, the constant current circuit 43 supplies a given constant current to the sensor element 31.

The constant current circuit 43 enables constant current Ics to flow from the exhaust side electrode 33 to the air side electrode 34 through the solid electrolyte layer 32 in the sensor element 31. Also the constant current circuit 43 has a PWM drive to enable adjustment of the amount of current by PWM control (duty control). The microcomputer 41 sets the amount of constant current (amount of energization) for the constant current circuit 43 according to each energization request and controls the constant current circuit 43 so that the constant current Ics in the set amount of constant current flows.

In this embodiment, the constant current is controlled according to the gap between reaction equilibrium point A1 for outflow of oxygen and $NO_x$ outflow point A2 for outflow of $NO_x$ in the first catalyst 15a and particularly the constant current is controlled so that the equilibrium point A1 of gas reaction in the vicinity of the exhaust side electrode of the $O_2$ sensor 17 is the same as or near to $NO_x$ outflow point A2. This means that the output characteristic of the $O_2$ sensor 17 is changed with reference to the purification characteristic of the first catalyst 15a and when $NO_x$ flows out from the first catalyst 15a, the $O_2$ sensor 17 outputs a lean signal from the beginning of the outflow.

From the viewpoint of ensuring robustness in order to suppress $NO_x$ emissions, it is preferable that the equilibrium point of gas reaction in the vicinity of the exhaust side electrode of the $O_2$ sensor 17 be on a richer side of $NO_x$ outflow point A2 (see FIG. 5). Specifically, it is preferable that the equilibrium point be on a richer side by an excess air ratio λ of about 0.1 to 0.5% (more preferably, 0.1 to 0.3%) than $NO_x$ outflow point A2 to produce a slightly rich condition.

Next, abnormality diagnosis of output response of the $O_2$ sensor 17 will be described. In this embodiment, the condition to conduct abnormality diagnosis (diagnosis condition) is that fuel cut has been performed with the sensor electromotive force (output value of the $O_2$ sensor 17) not less than the first prescribed value (for example, 0.6 V) which is on a richer side of the stoichiometric value; when the condition is satisfied, abnormality diagnosis is conducted according to the mode in which the sensor electromotive force varies. Specifically, for abnormality diagnosis, taking, as a parameter for abnormality diagnosis, the amount of output variation within a given time period (equivalent to the speed of variation) in which the sensor electromotive force varies toward a lean value (approximately 0 V) after the start of fuel cut, whether or not the response of the $O_2$ sensor 17 is abnormal is diagnosed according to the abnormality diagnosis parameter.

Figure 7:
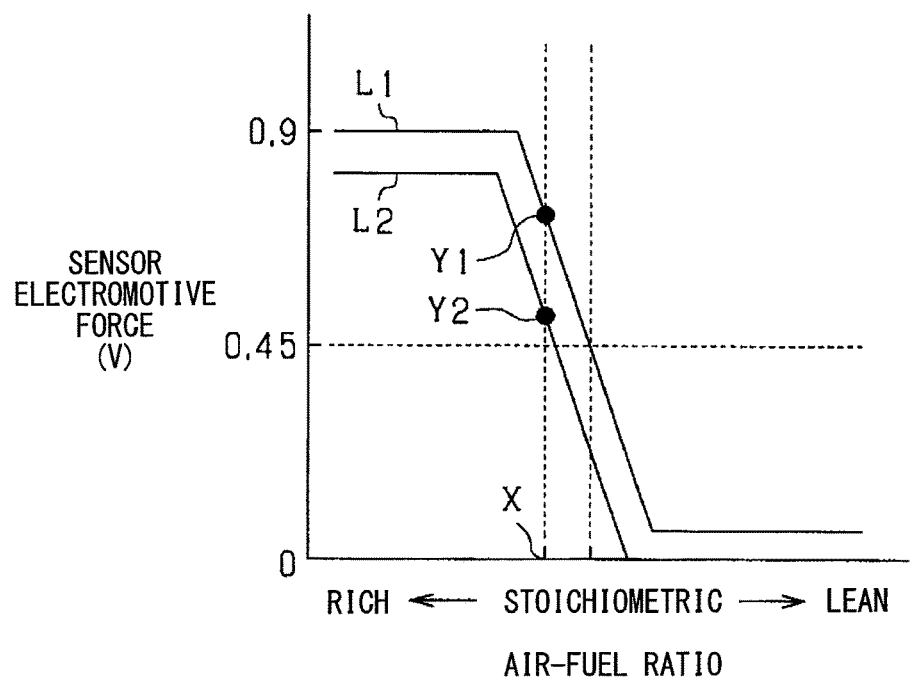
FIG. 7 is a graph which explains the sensor output characteristic when a prescribed constant current flows.

FIG. 7 is a graph which explains the sensor output characteristic in the case that the prescribed constant current Ics is supplied by the constant current circuit 43. In FIG. 7, L1 denotes the sensor output characteristic in an ordinary condition in which the constant current Ics does not flow and L2 denotes the sensor output characteristic in a condition in which the constant current Ics flows. For the convenience of explanation, output characteristic lines are indicated linearly in FIG. 7.

FIG. 7 shows a characteristic change in the case that the constant current flows in the $O_2$ sensor 17 in the direction in which oxygen pumping occurs from the air side electrode 34 to the exhaust side electrode 33 and indicates that L2, given the characteristic change, is wholly shifted to a richer side of L1. At this time, when the constant current Ics flows, the voltage changes depending on the internal resistance of the sensor element 31 (element resistance) and the constant current Ics supplied by the constant current circuit 43, and L2 indicates shift of the whole sensor electromotive force to the lower voltage side. In this case, in comparison in the sensor electromotive force at air-fuel ratio X richer than the stoichiometric ratio, whereas in ordinary output characteristic L1 the sensor electromotive force is "Y1", in output characteristic L2 the sensor electromotive force is "Y2" which is smaller than Y1.

As mentioned above, when the amount of output variation within the given time period with fuel cut is used as the abnormality diagnosis parameter, it is desirable to maximize the range of variation in the sensor electromotive force. However, as shown in FIG. 7, when the sensor electromotive force is smaller due to the supply of constant current Ics, the range of variation in the sensor electromotive force is smaller. In this case, the accuracy of abnormality diagnosis may decrease. In other words, the direction of increase/decrease in the sensor electromotive force with fuel cut and the direction of increase/decrease in the sensor electromotive force due to change in the sensor output characteristic with the supply of constant current Ics are both the direction of decrease in the sensor electromotive force (direction in which voltage drop occurs) and in such case, diagnosis accuracy may decrease due to the decrease in the range of variation in the sensor electromotive force.

Furthermore, in the arrangement that the condition to conduct abnormality diagnosis is that fuel cut has been performed with the sensor electromotive force not less than the first prescribed value on a richer side of the stoichiometric value, when the sensor electromotive force is small due to the supply of constant current Ics, the condition to conduct abnormality diagnosis would be hardly satisfied and the opportunity of abnormality diagnosis might be reduced (namely, the frequency of abnormality diagnosis might be decreased).

Therefore, in this embodiment, before conducting abnormality diagnosis of the $O_2$ sensor 17, the supply of constant current is temporarily stopped and abnormality diagnosis is conducted while the supply of constant current is stopped. Referring to FIG. 7, when the sensor electromotive force changes from Y1 to Y2 with the characteristic change due to the supply of constant current, the supply of constant current is stopped to return the sensor electromotive force to Y1 (increase its difference from the stoichiometric value when the sensor electromotive force is close to the stoichiometric value). Consequently, when abnormality diagnosis is conducted according to the mode (range of variation) in which the sensor electromotive force varies when the air-fuel ratio is changed to a lean one, the accuracy of the abnormality diagnosis is increased. Also, the possibility that the opportunity of abnormality diagnosis is unnecessarily reduced is suppressed.

Figure 8:
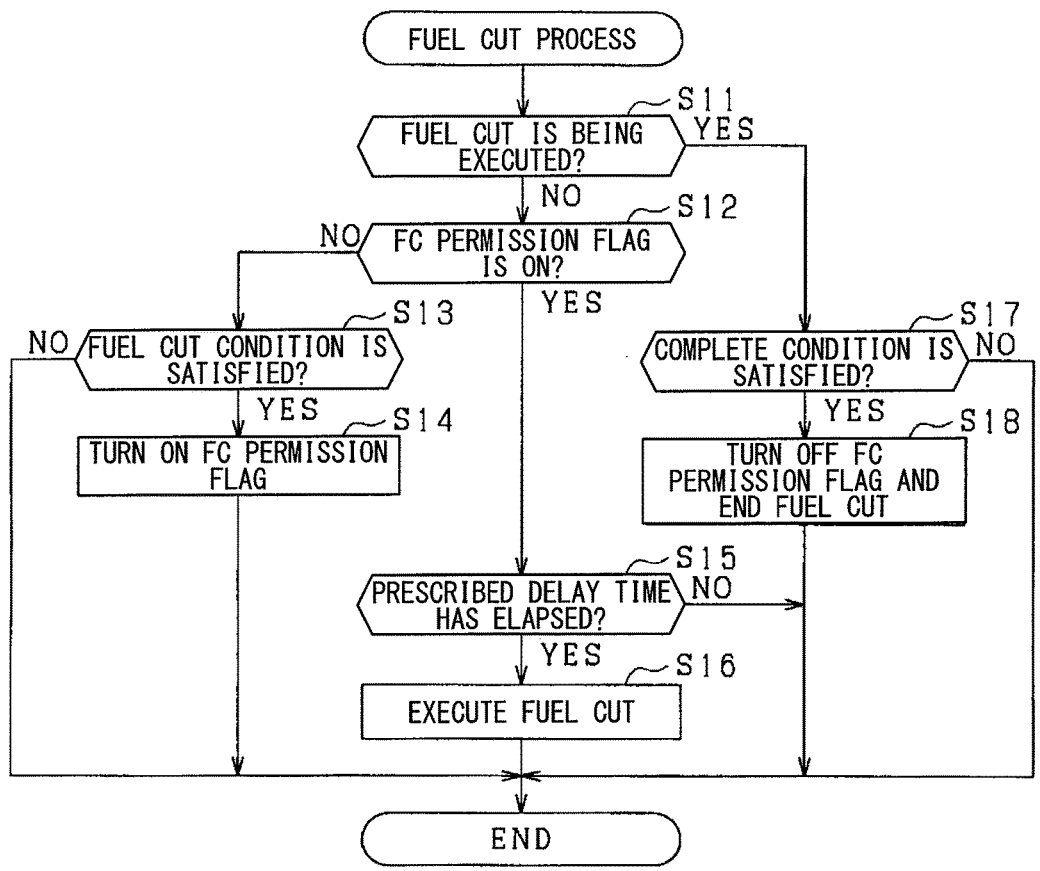
FIG. 8 is a flowchart which shows the fuel cut process.

Next, the fuel cut process and abnormality diagnosis process which are performed by the microcomputer 41 will be described in detail. FIG. 8 is a flowchart which shows the fuel cut process and this process is repeated by the microcomputer 41 in a given cycle.

In FIG. 8, at S11 the microcomputer 41 determines whether or not fuel cut is being executed. At S12, the microcomputer 41 determines whether or not an FC permission flag is on. The FC permission flag is a flag which represents permission to perform fuel cut. When YES at both S11 and S12, the microcomputer 41 proceeds to S13. At S13, the microcomputer 41 determines whether or not the known condition to perform fuel cut such as the accelerator off is satisfied. When the condition is satisfied, the microcomputer 41 proceeds to S14 and turns on the FC permission flag.

When NO at S11 and YES at S12, the microcomputer 41 proceeds to S15. At S15, the microcomputer 41 determines whether or not a prescribed delay time has elapsed since the FC permission flag was set. When the delay time has elapsed, the microcomputer 41 proceeds to S16 and executes fuel cut. In this embodiment, the step S16 corresponds to a fuel cut section. The delay time corresponds to a waiting time during which the start of fuel cut is suspended.

When YES at S11, the microcomputer 41 proceeds to S17. At S17, the microcomputer 41 determines whether or not the known condition to end fuel cut, such as that the accelerator is on and that the engine rotation speed drops to the value for stop of fuel cut, is satisfied. When the condition is satisfied, the microcomputer 41 proceeds to S18 and turns off the FC permission flag and ends fuel cut.

Figure 9:
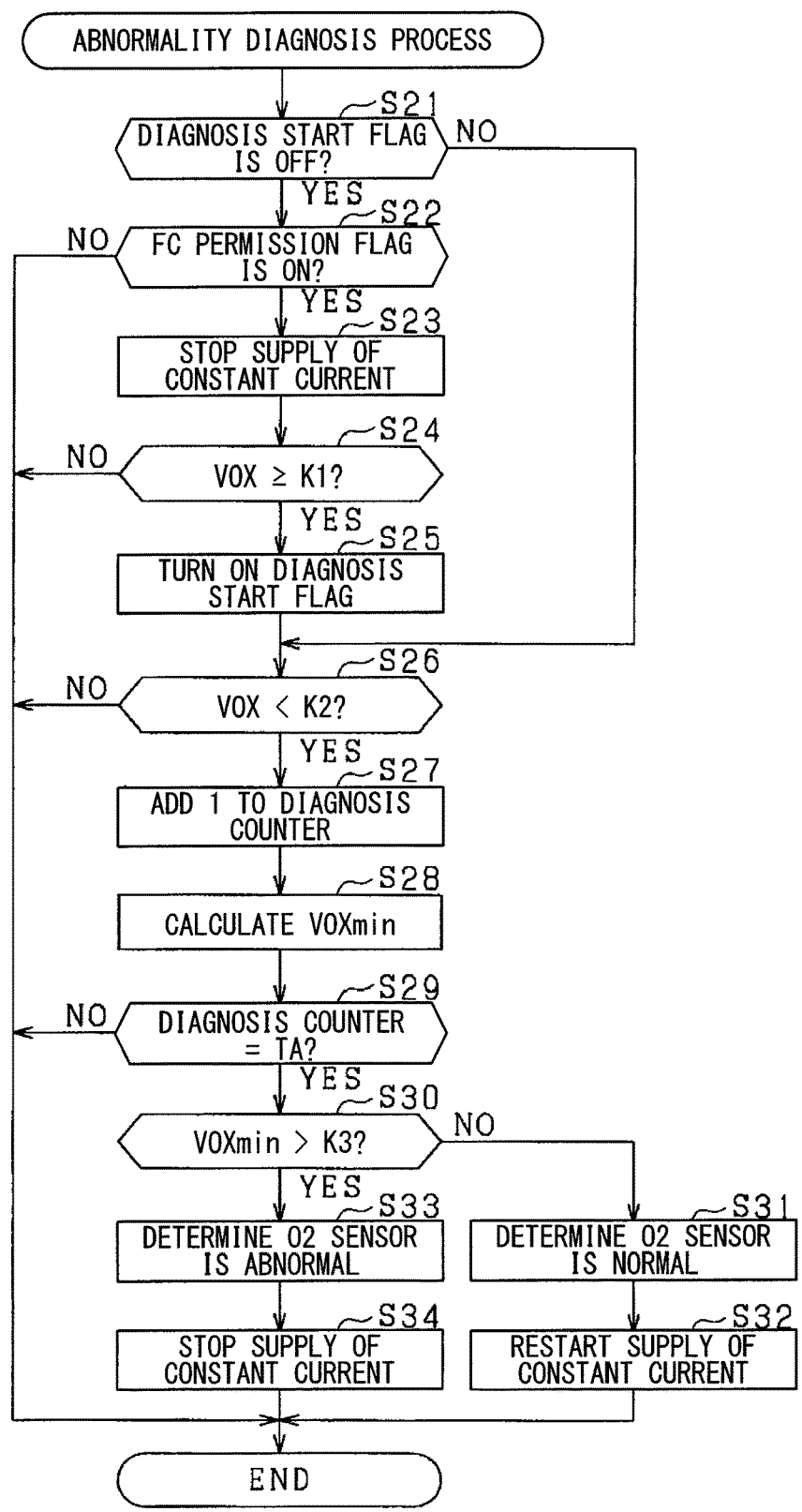
FIG. 9 is a flowchart which shows the abnormality diagnosis process.

FIG. 9 is a flowchart which shows the abnormality diagnosis process in this embodiment and this process is repeated by the microcomputer 41 in a given cycle.

In FIG. 9, at S21 the microcomputer 41 determines whether or not a diagnosis start flag indicating that abnormality diagnosis of the $O_2$ sensor 17 has been started is off. When abnormality diagnosis has not been started yet, the diagnosis start flag is off and the microcomputer 41 proceeds to S22. At S22, the microcomputer 41 determines whether or not the FC permission flag is on. When the FC permission flag is off, the microcomputer 41 ends the process or when the FC permission flag is on, the microcomputer 41 proceeds to the next step S23. At S23, the microcomputer 41 stops the supply of constant current Ics by the constant current circuit 43. In this embodiment, the step S23 corresponds to a control section.

After that, at S24 the microcomputer 41 determines whether or not the sensor electromotive force VOX is a first prescribed value K1 or more. The first prescribed value K1 is a value which is on a richer side of the stoichiometric value and for example, the first prescribed value K1 is 0.6 V. In this embodiment, the step S24 corresponds to a determining section. When VOX is less than the first prescribed value K1, the microcomputer 41 ends the process or when VOX is not less than the first prescribed value K1, the microcomputer 41 proceeds to the next step S25. At S25, the microcomputer 41 turns on the diagnosis start flag.

After that, at S26 the microcomputer 41 determines whether or not the sensor electromotive force VOX is less than a second prescribed value K2. The second prescribed value K2 is a value which is on a richer side of the stoichiometric value and on a leaner side of the first prescribed value K1 and for example, the second prescribed value K2 is 0.55 V. When VOX is the second prescribed value K2 or more, the microcomputer 41 ends the process or when VOX is less than the second prescribed value K2, the microcomputer 41 proceeds to the next step S27. When it is determined at S24 that VOX is the first prescribed value K1 or more, the answer at S26 should be negative. However, when fuel cut is started after the FC permission flag is turned on, and at S25 the sensor electromotive force VOX decreases, the answer at S26 is positive. At S27, the microcomputer 41 increments, by one, the diagnosis counter which measures the time after the sensor electromotive force VOX becomes less than the second prescribed value K2.

After that, at S28 the microcomputer 41 calculates the minimum value VOXmin of sensor electromotive force VOXmin from the sensor electromotive force VOX which is updated at regular time intervals. At this time, the microcomputer 41 may calculate VOXmin as follows: the previous VOX value and the present VOX value are compared and when the present value is smaller than the previous value, VOXmin is updated to the present value.

After that, at S29 the microcomputer 41 determines whether or not the reading of the diagnosis counter has reached a prescribed value TA. When the reading of the diagnosis counter is the prescribed value TA, the microcomputer 41 proceeds to S30 and determines whether or not the minimum value of sensor electromotive force VOXmin is larger than a prescribed abnormality threshold K3. The abnormality threshold K3 is a threshold to determine whether or not there is response abnormality of the O$_2$ sensor 17, according to the amount of variation in the sensor electromotive force within a given time period (within the prescribed TA period), and is defined as K2−α (for example, 0.1 V). In this case, when VOXmin is not larger than the abnormality threshold K3, it means that there is normal response change within the prescribed TA period and when VOXmin is larger than the abnormality threshold K3, it means that there is no normal response change within the prescribed TA period. In this embodiment, the step S30 corresponds to an abnormality diagnosing section. In sum, the steps S29 and S30 correspond to a process which determines the magnitude of the speed of decrease in sensor electromotive force VOX.

When VOXmin is not larger than the abnormality threshold K3, the microcomputer 41 proceeds to S31 and determines that the O$_2$ sensor 17 is normal. In this embodiment, the step S31 corresponds to an abnormality diagnosing section. At S32, the microcomputer 41 restarts the supply of constant current Ics by the constant current circuit 43. In this embodiment, the step S32 corresponds to a control section. When VOXmin is larger than the abnormality threshold K3, the microcomputer 41 proceeds to S33 and determines that the O$_2$ sensor 17 is abnormal. In this embodiment, the step S33 corresponds to an abnormality diagnosing section. At S34, the microcomputer 41 does not resume the supply of constant current Ics by the constant current circuit 43 but keeps the supply stopped. In this embodiment, the step S34 corresponds to a control section. The diagnosis start flag should be turned off when the FC permission flag is turned off.

In the diagnosis process in FIG. 9, it may be arranged that the step to measure the time after the start of fuel cut is added and when it is determined that VOXmin is larger than the abnormality threshold K3 (YES at S30) and the time after the start of fuel cut is longer than a prescribed time, the O$_2$ sensor 17 is determined as abnormal.

Figure 10:
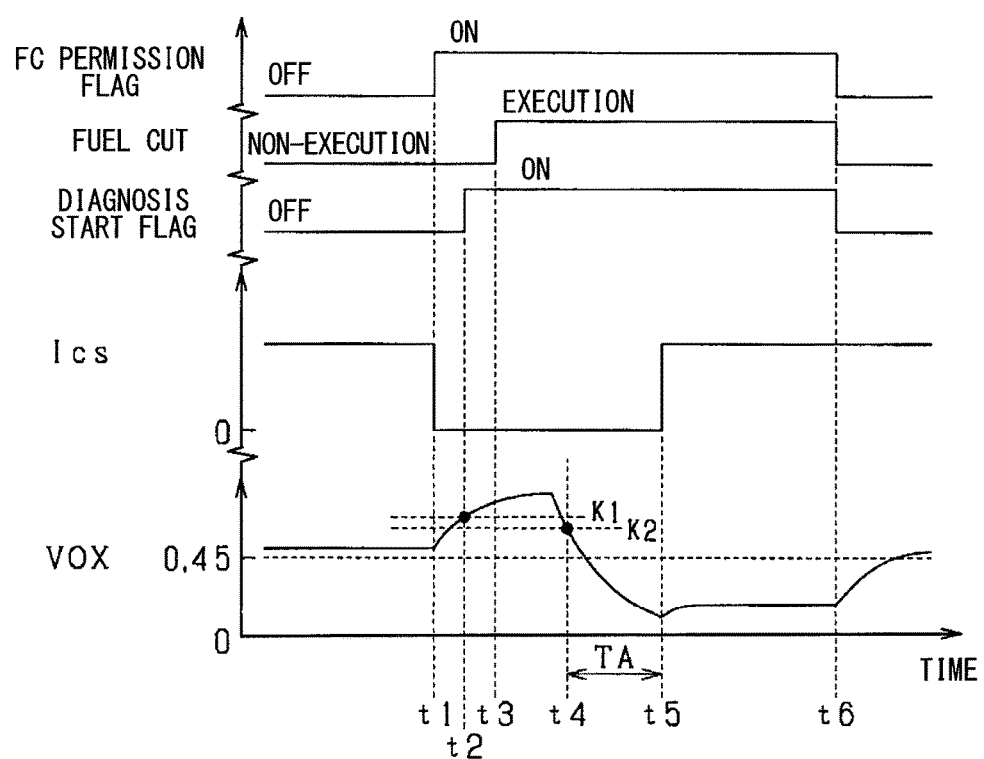
FIG. 10 is a time chart which shows abnormality diagnosis.

FIG. 10 is a time chart which shows abnormality diagnosis. In FIG. 10, before timing t1 the engine 10 is controlled so as to be in a normal combustion state and the constant current Ics is supplied from the constant current circuit 43 to the O$_2$ sensor 17 (sensor element 31). In this state, the air-fuel ratio is feedback-controlled so as to be nearly a stoichiometric ratio (specifically, slightly rich air-fuel ratio) and the sensor electromotive force VOX is nearly a stoichiometric value (for example, Y2 in FIG. 7). The supply of constant current to the O$_2$ sensor 17 should be continued after the O$_2$ sensor 17 comes to be in a prescribed activity state after start of the engine.

Then, when at timing t1 the fuel cut condition is satisfied by releasing the accelerator pedal, etc., the FC permission flag is set. As the flag is set, the supply of constant current Ics by the constant current circuit 43 is stopped. In this case, as the supply of constant current Ics is stopped, the characteristic change given to the O$_2$ sensor 17 is cancelled and the sensor electromotive force VOX gradually increases. Referring to FIG. 7, the sensor electromotive force changes from Y2 to Y1.

When the fuel cut condition is satisfied, even when the sensor electromotive force VOX is less than the first prescribed value K1 (0.6 V), at timing t2 the sensor electromotive force VOX is increased to the first prescribed value K1 or more by stopping the supply of constant current Ics. Consequently, the diagnosis start flag is set. Then, at timing t3 which is a prescribed delay time after timing t1, fuel cut is started. Thus the step to delay the start of fuel cut corresponds to waiting for the sensor electromotive force VOX to increase as a result of stopping the supply of constant current, before starting fuel cut. After fuel cut is started, the sensor electromotive force VOX begins to decrease after delay in transportation of exhaust gas, etc. occurs.

Then, at timing t4 the sensor electromotive force VOX becomes less than the second prescribed value K2 and after t4, VOXmin is calculated sequentially. After that, at timing t5, time at which the period of the prescribed value TA has elapsed after timing t4, response abnormality diagnosis of the O$_2$ sensor 17 is conducted according to VOXmin at that time.

At timing t5, the supply of constant current Ics is resumed and accordingly the sensor electromotive force VOX increases by the amount equivalent to the voltage variation with the supply of constant current Ics. At timing t6, as the condition to end fuel cut is satisfied, fuel cut is ended and ordinary combustion of the engine 10 is resumed. At timing t6, the FC permission flag and diagnosis start flag are turned off.

According to the embodiment detailed above, the following advantageous effects are brought about.

The supply of constant current is stopped before abnormality diagnosis of the $O_2$ sensor 17 is started. In other words, abnormality diagnosis of the $O_2$ sensor 17 is conducted after the supply of constant current is stopped. Therefore, in abnormality diagnosis, the range of variation in the sensor electromotive force can be larger than when the constant current is supplied. In this case, the desired range of variation in the sensor electromotive force can be ensured and the accuracy of abnormality diagnosis can be increased.

The diagnosis condition is that fuel cut has been performed with the sensor electromotive force not less than the first prescribed value K1 which is on a richer side of the stoichiometric value, and when it is determined that the diagnosis condition is satisfied, abnormality diagnosis is conducted. Consequently the range of variation in the sensor electromotive force can be sufficient for abnormality diagnosis and the reliability of abnormality diagnosis can be increased.

When the diagnosis condition includes a condition that fuel cut has been performed with the sensor electromotive force not less than the first prescribed value K1 on a richer side, the opportunity of abnormality diagnosis might be reduced (namely, the frequency of abnormality diagnosis might be decreased). In this respect, since the supply of constant current is stopped before abnormality diagnosis is conducted, it is easier to obtain a sensor electromotive force not less than the first prescribed value K1 and the possibility that the opportunity of abnormality diagnosis is unnecessarily reduced is suppressed.

In the arrangement that abnormality diagnosis of the $O_2$ sensor 17 is conducted during fuel cut, fuel cut is started after waiting for electromotive force output to increase in response to stop of the supply of constant current, which makes it certain that the sensor electromotive force is the first prescribed value K1 or more during fuel cut and ensures the opportunity to conduct abnormality diagnosis.

Since during fuel cut the supply of constant current is permitted upon completion of abnormality diagnosis, when the engine 10 is restored to a combustion state after the end of fuel cut, the desired air-fuel ratio control can be performed immediately after the restoration.

According to the control of the supply of constant current as mentioned above, the air-fuel ratio at which $NO_x$ begins to flow out in the first catalyst 15a can be combined with the output characteristic of the $O_2$ sensor 17. In short, when $NO_x$ flows out from the first catalyst 15a, electromotive force output of the $O_2$ sensor 17 which corresponds to the outflow can be generated. As a consequence, the output characteristic of the $O_2$ sensor 17 can be changed appropriately and $NO_x$ emissions can be suppressed.

Thus, $NO_x$ emissions can be suppressed (namely, optimization of the sensor output characteristic) by changing the sensor output characteristic and at the same time abnormality diagnosis can be conducted properly by restricting the supply of constant current during abnormality diagnosis as mentioned above.

Furthermore, according the constant current Ics supplied by the constant current circuit 43, the equilibrium point of gas reaction in the vicinity of the exhaust side electrode of the $O_2$ sensor 17 is shifted to the $NO_x$ outflow point A2 (second air-fuel ratio point) or its vicinity. Consequently a more suitable structure can be realized to suppress $NO_x$ emissions using output of the $O_2$ sensor 17.

Particularly, since the constant current Ics is supplied by the constant current circuit 43 so that the equilibrium point A1 of gas reaction in the vicinity of the exhaust side electrode of the $O_2$ sensor 17 is on a slightly richer side of $NO_x$ outflow point A2 (second air-fuel ratio point), robustness is ensured for suppression of $NO_x$ emissions.

Other Embodiments

The above embodiment may be altered as follows.

(a) In the above embodiment, when conducting abnormality diagnosis, the supply of constant current Ics is restricted by stopping the constant current Ics from the constant current circuit 43; however, this arrangement may be altered so that the supply of constant current Ics is restricted by decreasing the constant current Ics. For example, the supply of constant current Ics may be restricted by decreasing the constant current Ics to one half, one third or the like.

(b) In the above embodiment, abnormality diagnosis of the $O_2$ sensor 17 is conducted when the sensor electromotive force output varies with fuel cut; however this arrangement may be altered. For example, abnormality diagnosis may be conducted except when fuel cut is underway, or abnormality diagnosis may be conducted when the decrease in the amount of fuel injection causes the air-fuel ratio to shift to the lean side.

Also, abnormality diagnosis of the $O_2$ sensor 17 may be conducted according to the state of variation in the sensor electromotive force not only when the air-fuel ratio shifts to the lean side but also when the air-fuel ratio shifts to the rich side. Also the constant current circuit 43 may supply a constant current in a direction in which the sensor output characteristic is shifted to the lean side (direction in which the sensor electromotive force is increased). In any case, when the direction of increase/decrease in the sensor electromotive force during abnormality diagnosis is the same as the direction of increase/decrease in the sensor electromotive force due to the change in the sensor output characteristic with the supply of constant current, the supply of constant current should be stopped in conducting abnormality diagnosis.

Figure 11:
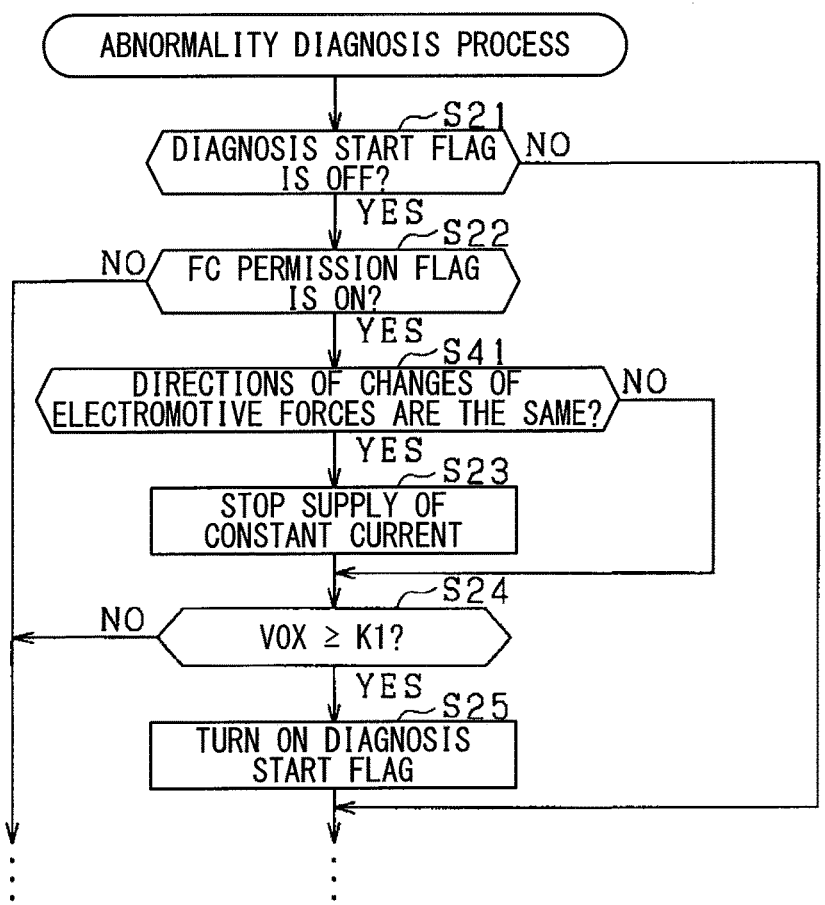
FIG. 11 is a flowchart which shows part of the abnormality diagnosis process.

(c) It may be arranged that determination is made as to whether or not the direction of increase/decrease in the sensor electromotive force during abnormality diagnosis of the $O_2$ sensor 17 is the same as the direction of increase/decrease in the sensor electromotive force due to the change in the sensor output characteristic with the supply of constant current, and when the directions are the same, the supply of constant current is stopped. Specifically, the process in FIG. 11 may be performed by the microcomputer 41. FIG. 11 shows only a relevant part of a partially modified version of FIG. 9.

In FIG. 11, when the diagnosis start flag is off and the FC permission flag is on, at S41 determination is made as to whether or not the direction of increase/decrease in the sensor electromotive force with fuel cut is the same as the direction of increase/decrease in the sensor electromotive force due to the change in the sensor output characteristic with the supply of constant current Ics, and when the directions are the same, the microcomputer 41 proceeds to S23 and stops the supply of constant current. When the directions of variation in electromotive force are different, S23 is skipped (namely, the supply of constant current is stopped).

(d) In the above embodiment, the amount of output variation within a prescribed time period (in the period in which the diagnosis counter corresponds to the prescribed value TA) is used as the abnormality diagnosis parameter (the state of variation in electromotive force output); however, this arrangement may be altered. For example, it may be arranged that the required time for the sensor electromotive force VOX to change from the second prescribed value K2 to the abnormality threshold K3 (time to change from the second prescribed value K2 to the abnormality threshold K3) is taken as the abnormality diagnosis parameter and when the required time is a prescribed value or more, it is determined that response abnormality has occurred.

(e) The delay time from when the fuel cut condition is satisfied until the start of fuel cut (delay time at S15 in FIG. 8) may be set as a variable. Specifically, at S15 in FIG. 8, the delay time may be set as a variable according to the constant current Ics at the time when the fuel cut condition is satisfied. In this case, as shown in FIG. 12(a), when the constant current Ics at the time when the fuel cut condition is satisfied is larger, the delay time should be longer. Alternatively, at S15 in FIG. 8, the delay time may be set as a variable according to the sensor electromotive force VOX at the time when the fuel cut condition is satisfied. In this case, as shown in FIG. 12(b), when the sensor electromotive force VOX is larger when the fuel cut condition is satisfied, the delay time should be shorter. By setting the delay time as a variable, abnormality diagnosis can be started with an appropriate waiting time for each condition to ensure that the time for abnormality diagnosis is available during fuel cut. That the sensor electromotive force VOX is large when the fuel cut condition is satisfied means that the difference between VOX and the first prescribed value K1 (K1−VOX) is large.

Alternatively, the delay time may be set according to the engine operation condition (engine rotation speed or engine load) at the time or just before the fuel cut condition is satisfied. In this case, the delay time should be shorter at higher rotation or higher load.

(f) Instead of the arrangement that fuel cut is performed after waiting for the prescribed delay time to elapse after the fuel cut condition is satisfied, it may be arranged that fuel cut is performed on the basis that the sensor electromotive force VOX is determined to be the first subscribed value K1 or more.

(g) In the arrangement that the supply of constant current is stopped (restricted) during fuel cut to conduct abnormality diagnosis, the supply of constant current may be resumed (the restriction is cancelled) at the end of fuel cut (for example, t6 in FIG. 10).

(h) In the above embodiment (FIG. 2), the constant current circuit 43 is connected to the air side electrode 34 of the paired electrodes 33 and 34 of the sensor element 31; however, this arrangement may be altered. The constant current circuit 43 may be connected to the exhaust side electrode 33. Alternatively the constant current circuit 43 may be connected to both the paired electrodes 33 and 34.

(i) Although the $O_2$ sensor 17 is located downstream of the first catalyst 15a in the above embodiment, instead the $O_2$ sensor 17 may be located in the middle portion of the first catalyst 15a. In this case, the $O_2$ sensor 17 may be located on the support of the first catalyst 15a. In short, the $O_2$ sensor 17 has only to take the exhaust gas purified by the first catalyst 15a as the object of detection and detect the gas components.

(j) The gas sensor is not limited to the above $O_2$ sensor 17, but instead the gas sensor may be a so-called 2-cell gas sensor which includes an electrogenic cell and a pump cell. In this case, the output characteristic of the electrogenic cell of the 2-cell gas sensor can be changed appropriately.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:
a constant current supply circuit configured to supply a constant current to the electromotive cell; and
a computer comprising a memory storing computer code and a hardware processor for executing the computer code so that the computer is at least configured to perform:
a control for controlling the constant current supply circuit to supply the constant current to the electromotive cell in order to change an output characteristic of the electromotive cell; and
an abnormality diagnosis of an output response of the electromotive cell on the basis of a state of variation in an electromotive force output, when the electromotive force output of the electromotive cell varies, wherein
when the abnormality diagnosis is conducted, the control restricts a supply of the constant current by the constant current supply circuit before conducting the abnormality diagnosis,
the constant current supply circuit supplies the constant current so that the output characteristic is changed to a lean side or a rich side; and
when the direction of increase/decrease in the electromotive force output during abnormality diagnosis is the same as the direction of increase/decrease in the electromotive force output due to change in the sensor output characteristic with the supply of the constant current, the control stops the supply of the constant current in the abnormality diagnosis.

2. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:
a constant current supply circuit configured to supply a constant current to the electromotive cell; and
a computer comprising a memory storing computer code and a hardware processor for executing the computer code so that the computer is at least configured to perform:

a control for controlling the constant current supply circuit to supply the constant current to the electromotive cell in order to change an output characteristic of the electromotive cell; and an abnormality diagnosis of an output response of the electromotive cell on the basis of a state of variation in an electromotive force output, when the electromotive force output of the electromotive cell varies, wherein when the abnormality diagnosis is conducted, the control restricts a supply of the constant current by the constant current supply circuit before conducting the abnormality diagnosis;

the gas sensor control device is for a control system in which a fuel cut of the internal combustion engine is performed on the basis of a fuel cut condition;

the computer is further configured to perform a determination which determines whether or not a diagnosis condition is satisfied, the diagnosis condition being that the fuel cut has been performed with the electromotive force output not less than a certain value on a richer side of a stoichiometric value;

one of the paired electrodes in the electromotive cell is a reference side electrode that is positive in polarity with respect to the electromotive force output and the other is an exhaust side electrode that is negative in polarity with respect to the electromotive force output;

the constant current supply circuit supplies the constant current from the exhaust side electrode to the reference side electrode through the solid electrolyte body in the electromotive cell; and the computer is further configured to conduct the abnormality diagnosis when the determination determines that the diagnosis condition is satisfied.

3. The gas sensor control device according to claim 2, further comprising:

the computer is further configured to perform the fuel cut after the electromotive force output increases to the certain value or more with a restriction of the supply of the constant current executed by the control, in a case where the fuel cut condition is satisfied.

4. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:

a constant current supply circuit configured to supply a constant current to the electromotive cell; and a computer comprising a memory storing computer code and a hardware processor for executing the computer code so that the computer is at least configured to perform:

a control for controlling the constant current supply circuit to supply the constant current to the electromotive cell in order to change an output characteristic of the electromotive cell; and an abnormality diagnosis of an output response of the electromotive cell on the basis of a state of variation in an electromotive force output, when the electromotive force output of the electromotive cell varies, wherein when the abnormality diagnosis is conducted, the control restricts a supply of the constant current by the constant current supply circuit before conducting the abnormality diagnosis;

the gas sensor control device further comprises a catalyst located in an exhaust part of the internal combustion engine, the catalyst purifying: (i) NOx that is a lean component in the exhaust gas and (ii) a rich component in the exhaust gas;

the gas sensor is located in a middle portion of the catalyst or downstream of the catalyst and is applied to an exhaust gas purifying device of the internal combustion engine detecting an air-fuel ratio of the object of the detection which is the exhaust gas after being purified by the catalyst;

the catalyst has a purification characteristic indicating a relation between air-fuel ratio and purification rate, and in the purification characteristic, a second air-fuel ratio point at which the NOx begins to flow out is on a richer side of a first air-fuel ratio point as an equilibrium point of the rich component and oxygen; and the control performed by the computer uses a current corresponding to a gap between the first air-fuel ratio point and the second air-fuel ratio point as the constant current and controls the constant current supply circuit to perform the supply of the constant current.

* * * * *